United States Patent [19]

Lotze

[11] 4,207,162
[45] Jun. 10, 1980

[54] CHEMICAL DETECTOR UTILIZING AN ELECTROLYTIC GEL

[75] Inventor: Thomas H. Lotze, Peekskill, N.Y.

[73] Assignee: Cambridge Instrument Company, Inc., Ossining, N.Y.

[21] Appl. No.: 18,154

[22] Filed: Mar. 7, 1979

[51] Int. Cl.² ........................................... G01N 27/46
[52] U.S. Cl. ............................... 204/195 R; 204/1 T
[58] Field of Search ............. 204/1 N, 195 R; 324/29

[56] References Cited

U.S. PATENT DOCUMENTS

| | | | |
|---|---|---|---|
| 2,183,531 | 12/1939 | Allison | 204/195 F X |
| 2,651,612 | 9/1953 | Haller | 204/195 R |
| 3,000,804 | 9/1961 | Cahoon et al. | 204/195 F |
| 3,671,414 | 6/1972 | Grubb | 204/195 R |
| 3,694,338 | 9/1972 | Weingarten | 204/195 R |
| 3,833,495 | 9/1974 | Grubb | 204/195 F |
| 3,957,612 | 5/1976 | Niedrach et al. | 204/195 M |
| 3,957,613 | 5/1976 | Macur | 204/195 M |
| 4,105,509 | 8/1978 | Jungck | 204/1 T |

*Primary Examiner*—G. L. Kaplan
*Attorney, Agent, or Firm*—Eugene E. Geoffrey, Jr.

[57] ABSTRACT

A detector for reducing and oxidizing agents carried by fluids which detector includes an elongated exposed porous member having an opening extending therethrough, an electrolyte gel containing a metal salt filling said opening, a first metal electrode extending through said gel and a metal electrode on the outer side of said porous member, the porous member and electrode upon being placed in the path of the fluid will cause a current to be developed between the electrodes which is proportional to the amount of chemical in said fluid. The detector is especially useful for the detection of hydrazine in boiler feed water.

2 Claims, 3 Drawing Figures

U.S. Patent
Jun. 10, 1980
4,207,162
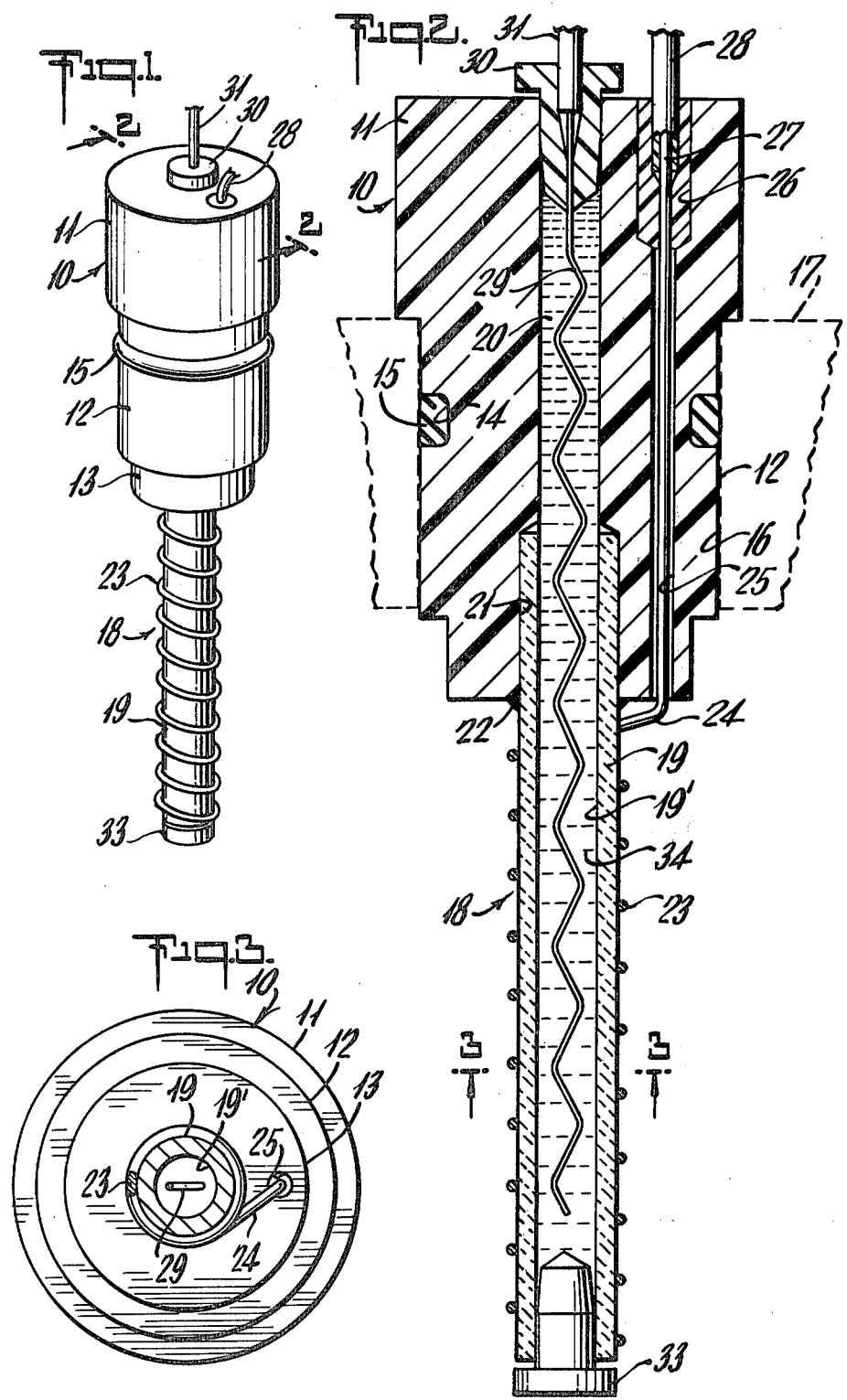

CHEMICAL DETECTOR UTILIZING AN ELECTROLYTIC GEL

This invention relates to a chemical detector and more specifically to a novel and improved detector for detection of the presence of chemicals in fluids and is particularly useful for the detection of hydrazine in boiler feed water.

Prior known devices for the detection of reducing and oxidizing agents and more specifically hydrazine in water have generally embodied an arrangement utilizing an elongated porous tube having a platinum electrode wound about the outer surface thereof, an inner silver electrode extending into or in close proximity to the porous tube and means for feeding liquid electrolyte together with silver oxide into the tube to saturate the tube and contact the external electrode. With this arrangement, a gas or liquid contacting the external electrode and carrying a chemical such as hydrazine in water to be detected produces an electrical reaction and causes a current to flow between the silver and platinum electrodes. This current is proportional to the quantity of the chemical being detected and is measured by a suitable indicator.

This invention overcomes the disadvantages heretofore encountered with the general class of detectors described above and provides a novel and improved detector utilizing an electrolytic gel which avoids the use of dangerous caustic solutions, minimizes the loss of electrolyte and maintains the metal oxide in suspension within the porous tube.

Another object of the invention resides in the provision of a novel and improved detector for hydrazine and other oxidizing and reducing agents which is characterized by its simplicity, safety and ease of maintenance.

Still another object of the invention resides in a novel and improved detector for oxidizing and reducing agents carried by fluids.

The detector in accordance with the invention includes an elongated hollow porous member carried by and extending from a support. A wire electrode is wound about the outer side of the porous member, a second electrode is disposed within said member and a gel electrolyte having a metal oxide suspended therein fills said porous member and surrounds the electrode positioned therein.

The above and other objects and advantages of the invention will become apparent from the following description and accompanying drawings forming part of this application.

IN THE DRAWINGS

FIG. 1 is a perspective view of a detector in accordance with the invention;

FIG. 2 is an enlarged cross sectional view of FIG. 1 taken along the line 2—2 thereof and FIG. 3 is a cross sectional view of FIG. 2 taken along the line 3—3 thereof.

Referring now to the drawing, FIG. 1 is a full scale view of the detector in accordance with the invention and comprises a body portion 10 preferably formed of an insulating material and having a cylindrical upper portion 11 and a lower portion 12 of slightly reduced diameter and which terminates in a relatively short portion 13 of somewhat smaller diameter than the portion 12. The portion 12 of reduced diameter has an annular groove 14 as seen more clearly in FIG. 2 to accommodate an O-ring 15 of a resilient material. The body as shown in FIG. 1 is adapted to be received in an opening 16 in a fluid carrying conduit 17 and the O-ring 15 effects a seal between the body 10 and the conduit 17.

The detecting element is generally denoted by the numeral 18 and comprises a porous tube 19 of ceramic material or the like which extends within an enlarged portion 21 of an opening 20 which extends through the body portion 10. The porous tube 19 may be secured to the body in any suitable manner as for instance through the utilization of an appropriate cement 22.

A first electrode 23 is in a form of a helix wound about the outer side of the tube 19. The upper end 24 of electrode 23 extends upwardly through an opening 25 in the body 10 and terminates in an enlarged opening portion 26 where it is soldered or otherwise secured to the conductor 27 having an insulating sheath 28. The opening 26 is then filled with a suitable cement.

A second electrode 29 extends downwardly through the opening 20 in the body portion 10 and through the porous structure 19 to a point spaced from the bottom end thereof. This electrode may have a zig-zag or coiled configuration in order to provide adequate surface within the porous structure 19.

The upper end of the electrode 29 extends into a plug 30 of resilient material which has an opening therein to accommodate the upper end of the electrode 29. A second insulated lead 31 extends into the upper side of the plug 30 and the conducting element 32 within the lead 31 is soldered or otherwise secured to the upper end of the electrode 29. The bottom end of the porous structure 19 is closed by a resilient plug 33.

The opening 20 and the opening 19' within the porous member 19 are preferably filled with an electrolytic gel 34 having a metallic oxide held in suspension therein. In the case of hydrazine, for instance, the helical electrode 23 is preferably formed of platinum, the electrode 29 is formed of silver and the gel 34 includes the following constituents:

Silver Oxide 3% to 10% by weight
Hydroxy-ethyl Cellulose 1% to 3% by weight
Distilled Water The pH of the solution is preferably adjusted if necessary to 7.5 to 8.5 by the addition of sulphuric acid.

In operation, the process which occurs in the detection of dissolved hydrazine is as follows:

$$N_2H_4 + 2Ag_2O \rightarrow N_2 + 4Ag + 2H_2O$$

This results from the following reactions occurring at the platinum anode and silver cathode:

$$N_2H_4 + 4OH^- \rightarrow N_2 + 4H_2O + 4e^- \quad (anode)$$

$$4e^- + 2Ag_2O + 2H_2O \rightarrow 4Ag + 4OH^- \quad (cathode)$$

The current produced by the cell causes depletion of hydrazine and hydroxyl ions at the anode and creation of hydroxyl ions at the cathode. This will have little influence on the pH at the platinum wire anode since the sample water will normally be well-buffered at 8.5 to 10 pH. The pH at the cathode will rise, however, until there is sufficient pH across the ceramic to provide $OH^-$ diffusion to match the current flow, that is, one $OH^-$ ion per electron. Silver oxide molecules will also migrate to the silver cathode and the hydroxy-ethyl cellulose solution provides the matrix in which these migrations occur.

The utilization of the gel as described above provides virtually linear operation in the range of 0 to 500 PPB hydrazine. This linearity occurs by reason of the use of the gel which causes the controlling migration, that is, diffusion of the hydrazine at the platinum anode. Without the use of the gel electrolyte, substantial non-linearities would be observed at the higher concentrations. Moreover, a relatively high sensitivity of the order of 56 nano amps per PPB is attained at about 25° C.

The gel electrolyte has a still further advantage in that it materially retards depletion of the silver oxide through the porous member which is an essential component of the cell. Moreover, the gel avoids the need for caustic solutions heretofore employed so that maintenance of the cell can be effected without any danger whatsoever. To replace the gel, the plug 30 and electrode 29 are removed from one end of the cell and the plug 33 from the other end. The gel is then washed out, plug 33 is replaced, a fresh gel is then introduced preferably to fill openings 20 and 19' in the body portion 11 and the porous member 19 and electrode 29 and plug 30 are replaced.

The indicating means may take any suitable form well known in the art for use with current generating cells of the types disclosed herein. For instance, the leads 28 and 31 would preferably be connected to a very low value resistor so that the current produced by the cell will produce a voltage across the resistor. This voltage is then amplified and an indicator connected to the output of the amplifier is arranged to provide an indication in PPB. Since the cell in accordance with the invention is virtually linear over the desired range of operation, a linear amplifier can be used and calibration of the indicator is greatly simplified.

While only one embodiment of the invention is illustrated and described, it is apparent that alterations, changes and modifications may be made without departing from the true scope and spirit thereof.

What is claimed is:

1. An electrolytic cell for the detection of hydrazine in water comprising an elongated hollow cylindrical member formed of a porous insulating material, insulating means for supporting said member in said water, a platinum electrode wound about the outer side of said member and having a lead wire extending therefrom, a silver electrode within said member and having a lead wire extending therefrom, an electrolytic gel containing silver oxide at least partially filling said member and enveloping said silver electrode and indicating means connected between said lead wires, said indicating means responding to the current flowing between said electrodes when hydrazine is present in the water.

2. An electrolytic cell according to claim 1 wherein said gel includes:
   Silver oxide 3% to 10% by weight
   Hydroxy-ethyl cellulose 1% to 3% by weight
   Distilled water balance

* * * * *